United States Patent [19]

Hammar

[11] 3,950,407

[45] Apr. 13, 1976

[54] PROCESS FOR PREPARING DIBENZO[A,D]CYCLOHEPTENES

[75] Inventor: Walton J. Hammar, St. Paul, Minn.

[73] Assignee: Riker Laboratories, Incorporated, Northridge, Calif.

[22] Filed: June 18, 1973

[21] Appl. No.: 371,118

[52] U.S. Cl....... 260/515 R; 260/343.3 R; 260/349; 260/471 A; 260/471 C; 260/473 F; 260/475 SC; 260/570.8 R
[51] Int. Cl.$^2$...................................... C07C 63/595
[58] Field of Search ............................... 260/515 R Primary Examiner—James A. Patten
Attorney, Agent, or Firm—Alexander, Sell, Steldt & DeLaHunt

[57] ABSTRACT

The maleic acid adduct of anthracene is used as a starting material for 11-amino-12-carboalkoxy-9,10-dihydro-9,10-ethanoanthracene, which through reaction with nitrous acid in a protic solvent provides an 11-substituted-12-carboalkoxy-10,11-dihydro-5,10-methano-5H-dibenzo[a,d]cycloheptene which is then converted into the useful intermediate 12-carboxy-10,11-dihydro-5,10-methano-5H-dibenzo[a,d]cycloheptene.

4 Claims, 1 Drawing Figure

PROCESS FOR PREPARING
DIBENZO[A,D]CYCLOHEPTENES

BACKGROUND OF THE INVENTION

The compound 12-carboxy-10,11-dihydro-5,10-methano-5H-dibenzo[a,d]cycloheptene (I) is a known intermediate compound in a process for preparation of pharmacologically active 10,11-dihydro-12-(substituted aminoalkyl)-5,10-methano-5H-dibenzo[a,d]-cycloheptenes. (See U.S. patent application Ser. No. 194,056 or German Offenlegungschrift No. 2,216,884.) The novel route of this invention for preparing this valuable intermediate employs several novel intermediates.

References useful to show the state of the art include S. Wawzonek et al, J. Org. Chem. 18, 288 (1953); W. R. Vaughan et al, J. Am. Chem. Soc. 80, 1956 (1958); C.A. 61, 6971f, thesis of D. E. Plorde and C. A. 61, 14551, thesis of J. Mohrig.

DETAILED DESCRIPTION OF THE INVENTION

Figure 1:
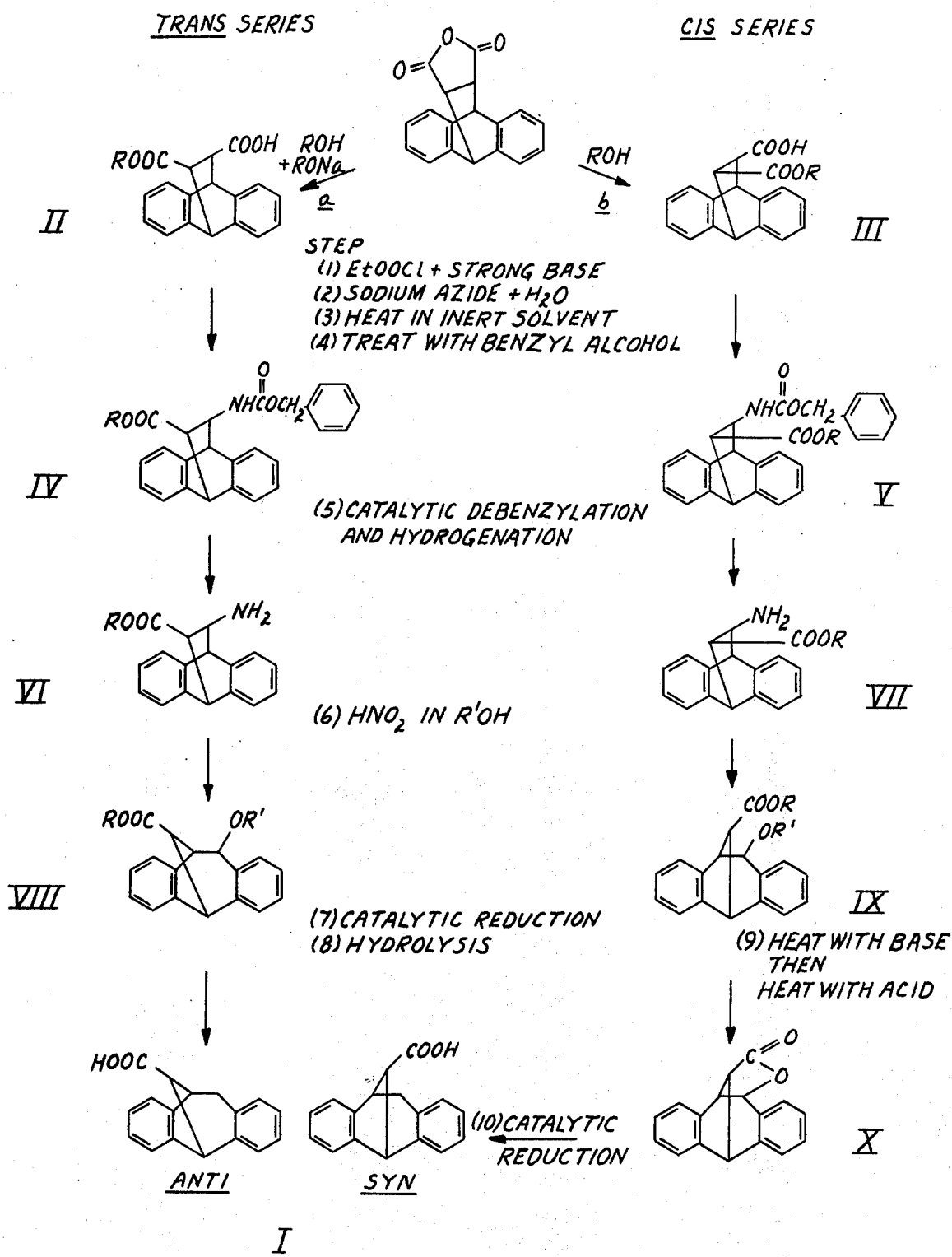

This invention relates to the process wherein 12-carboxy-10,11-dihydro-5,10-methano-5H-dibenzo[a,d]cycloheptene (Compound I) is first prepared and the intermediate is used for preparation of 10,11-dihydro-12-(substituted aminoalkyl)-5,10-methano-5H-dibenzo[a,d]cycloheptenes having the desired substituents and structural configuration. Compound (I) is prepared by treating the maleic anhydride adduct of anthracene to make the novel intermediate 11-amino-12-carboalkoxy-9,10-dihydro-9,10-ethanoanthracene in a procedure involving several steps, from which, in two steps by reaction with nitrous acid in a protic solvent, is prepared an 11-substituted-12-carboalkoxy-10,11-dihydro-5,10-methano-5H-dibenzo[a,d]cycloheptene which is then converted to compound (I). Compound (I) can be prepared in either the syn or anti isomeric forms, and the routes to each are shown in the sequence of reactions set forth in the accompanying drawing, FIG. 1, wherein R represents lower alkyl and R' represents hydrogen, lower alkyl or lower acyl. "Lower" herein means having 1 to 6 carbon atoms and is preferably 1 to 3 carbon atoms.

The starting material for the process, the maleic anhydride adduct of anthracene, is known to the art, as are the cis and trans acid esters II and III and the lactone X. The other intermediate compounds produced in this process and shown in the reaction sequence are novel and comprise a part of the present invention.

When the maleic anhydride adduct of anthracene (which also can be termed 11,12-cis-dicarboxy-9,10-dihydro-9,10-ethano-anthracene) is reacted to produce the carboalkoxy ester-carboxy compound, it can be made to form the trans compound (II) or the cis compound (III) depending upon the reaction conditions. When the anhydride is treated with a lower alkanol in the presence of a strong base such as an alkali metal alkoxide, for example sodium methoxide or ethoxide as shown in step a, at a temperature of about 0° to 120° C. and preferably from about 20° to 90° C., the product isolated is the trans isomer. When heated in a lower alkanol such as methanol, ethanol or n-butanol as shown in step b, at a temperature of about 60° to 120° C., a cis ester of formula II is formed. Using the resulting cis- or trans-12-carboalkoxy-11-carboxy-9,10-dihydro-9,10-ethanoanthracene compounds of formula II or formula III, respectively, the carboxy group is (1) reacted with a lower alkyl chloroformate such as ethyl chloroformate in the presence of a strong base, such as triethylamine, trimethylamine, pyridine, N,N-dimethylaniline and the like, in an inert solvent such as acetone, benzene, chloroform, acetonitrile and the like, at a temperature of about −20° to 10° C., to provide the mixed anhydride derivative which is not isolated. The mixed anhydride derivative is (2) treated with aqueous sodium or potassium azide at a temperature of −20° to 25° C. to form the acyl azide derivative (generally a solid) which is further reacted (3) by heating at about 80° to 120° C. in an inert solvent such as toluene to give a rearrangement intermediate isocyanate. The isocyanate is (4) treated with benzyl alcohol at about 80° to 120° C. to provide a trans- or cis-11-(N-carbobenzyloxyamino)-12-carboethoxy-9,10-dihydro-9,10-ethanoanthracene compound of formula IV or V. The products of these steps need not be isolated and purified. It will be apparent that in the case of the azide it is removed from the reaction mixture in which it was formed, as by filtration.

The compound of formula IV or V is debenzylated by catalytic hydrogenation as shown in step (5). An inert solvent is conveniently used, for example ethyl acetate, methanol, ethanol and acetic acid. The preferred hydrogenation catalyst is palladium on charcoal. The temperature is generally about 25° C. but may range up to 100° C. to increase the rate of reaction. The product obtained is the key intermediate, trans- or cis-11-amino-12-carboalkoxy-9,10-dihydro-9,10-ethanoanthracene of formula VI or VII.

The compound of formula VI or VII is (6) reacted with nitrous acid in a protic solvent such as an alkanoic acid, e.g. acetic acid, propionic acid, trifluoroacetic acid or n-butyric acid, an alcohol, e.g. methanol, ethanol or propanol, or an inorganic acid, e.g. aqueous hydrochloric acid or dilute sulfuric acid. The reaction temperature is between about 0° and 50° C. If an inorganic acid is used, or water is present, the substituent in the 8-position of the rearranged product will generally be hydroxy. It is presently preferred to use a lower alkanoic acid such as acetic acid or propionic acid as the solvent. Rearrangement to a cycloheptene structure occurs, and the rearrangement product is a 11-lower acyloxy-12-anti- or syn-lower carboalkoxy-10,11-dihydro-5,10-methano-5H-dibenzo[a,d]cycloheptene compound of formula VIII or IX wherein R' is hydrogen, lower alkyl or the acyl residue of an alkanoic acid.

The compound of formula VIII or IX is (7) catalytically reduced to remove the substituent from the 11-position. This reduction is generally carried out in an inert solvent, such as acetic acid, ethyl acetate and the like. The preferred catalyst is palladium on charcoal. The temperature is generally about 25° C., but may range up to 100° C. A catalytic amount of 70 percent perchloric acid is used. The carboxylic acid ester in the 12 position is then (8) saponified at 80° to 120° C. to complete the transformation. General saponification methods known to the art are used, preferably simple hydrolysis using aqueous alkali metal hydroxide such as sodium hydroxide. The product is the syn or anti isomer of compound I, 12-carboxy-10,11-dihydro-5,10-methano-5H-dibenzo[a,d]cycloheptene, depending on the starting compound employed.

As an alternative method useful in the case of the preparation of syn compounds, which provides higher yields and easier purification, compound IX may be (9)

converted to the corresponding known lactone by irst removing the R' substituent in the 11-position, then cyclizing. This is done by first heating at about 25° to 100° C. with aqueous inorganic base, for example 10 percent sodium hydroxide, to provide the hydroxy acid. (When R' is alkyl it may be advantageous to cleave the group to hydroxyl form by routine ether cleavage methods, such as treatment with aqueous hydroiodic acid at temperatures in the range of 25° to 100° C., since the alkoxy group will not be cleaved by base. This step is equivalent to using compound in which R' is hydrogen.) The intermediate hydroxy acid is then converted to the lactone X by heating at about 70° to 120° C. in an inert solvent such as toluene in the presence of a catalytic amount of an acid such a p-toluene sulfonic acid. The lactone X is (10) reduced catalytically as in step (7) in inert solvent solution, preferably using palladium on charcoal, to complete the conversion to syn formula I compound. An inert solvent such as ethyl acetate is preferred.

The compound of formula I, whether in the syn or anti form, is suitable for further reaction as described in the art to provide the pharmacologically active 10,11-dihydro-12-(substituted aminoalkyl)-5,10-methano-5H-dibenzo[a,d]cycloheptenes and their salts.

The following examples are provided to illustrate the process of the invention and preparation of the novel intermediate compounds of the invention and their salts, and are not intended to be limiting of the invention described hereinabove.

Example 1

A fresh batch of sodium ethoxide is prepared by reaction of 14 g. of sodium and 300 ml. of ethanol. To this solution is added in one batch 70 g. (0.253 mole) of 11,12-cis-dicarboxy-9,10-dihydro-9,10-etanoanthracene anhydride, and the mixture is stirred for 20 hours at about 25° C. The resulting solution is poured into 1.3 liters of ice water containing 100 ml. of concentrated hydrochloric acid. An oil separates and solidifies. The solid is separated by filtration, washed with water and dried to provide 72.7 g. of trans-12-carboethoxy-11-carboxy-9,10-dihydro-9,10-ethanoanthracene, m.p. 182°–184° C.

Analysis: Calculated for $C_{20}H_{18}O_4$: %C, 74.5; %H, 5.63. Found: %C, 74.5; %H, 5.80.

Example 2

A mixture of 1.5 liters of methanol and 70.5 g. (0.255 mole) of 11,12-cis-dicarboxy-9,10-dihydro-9,10-ethanoanthracene anhydride is heated at its reflux temperature for 21 hours. The mixture is evaporated under vacuum, and hexane is added to the residue. The residual oil slowly crystallizes, and the solid is separated by filtration to provide 61.1 g. of the known compound cis-12-carbomethoxy-11-carboxy-9,10-dihydro-9,10-ethanoanthracene.

Example 3

A solution of trans-12-carboethoxy-11-carboxy-9,10-dihydro-9,10-ethanoanthracene prepared as set forth in Example 1 (19.3 g., 60 mmoles) in 11 ml. of water and 100 ml. of acetone is cooled to 0° C. Ethyl chloroformate (8.6 g., 79 mmoles) in 30 ml. of acetone is added dropwise at 0° C., then the mixture is stirred at 0° C. for about thirty minutes. Sodium azide (6.2 g., 94 mmoles) in 20 ml. of water is added at 0° C., and the mixture is stirred at 0° C. for 1 hour, then poured into 500 ml. of ice water. The product is extracted twice with di-ethyl ether, the ether layers are washed with saturated sodium chloride solution, then dried over anhydrous magnesium sulfate. Evaporation under vacuum gives 19.7 g. of a white solid, trans-11-azido-12-carboethoxy-9,10-dihydro-9,10-ethanoanthracene.

The infrared spectral analysis of this compound is in agreement with the assigned structure. The solid azide is dissolved in 75 ml. of dry toluene and heated on a steam bath until the evolution of nitrogen stops. The toluene is removed by evaporation under vaccuum to provide 16.9 g. of a yellow oil. The oil is treated with 17.2 g. of benzyl alcohol, and the mixture is heated on a steam bath for 2 hours. The excess benzyl alcohol is removed by evaporation under vacuum leaving 22.7 g. of a yellow oil, trans-11-(N-carbobenzyloxyamino)-12-carboethoxy-9,10-dihydro-9,10-ethanoanthracene.

The oil is dissolved in 100 ml. of ethyl acetate, 5.0 g. of palladium on charcoal are added and the mixture is treated with hydrogen gas at about 45 psi on a Parr apparatus until uptake of hydrogen stops. The mixture is filtered, the filtrate is evapoated under vacuum, and the residue is disolved in diethyl ether. The ether solution is washed with saturated sodium bicarbonate solution and saturated sodium chloride solution, then dried over anhydrous magnesium sulfate to give 20.7 g. of an oil. The oil is dissolved in diethyl ether and extracted with 5 percent hydrochloric acid. The acid extracts are neutralized with sodium bicarbonate. The aqueous solution is extracted with diethyl ether, and the ether layer is dried over magnesium sulfate. The ether is removed by evaporation under vacuum to provide a solid residue which is recrystallized from a benzene-hexane mixture to provide trans-11-amino-12-carboethoxy-9,10-dihydro-9,10-ethanoanthracene, m.p. 118°–121° C.

Analysis: Calculated for $C_{19}H_{19}NO_2$: %C, 77.8; %H, 6.53; %N, 4.78 Found: %C, 78.1; %H, 6.50; %N, 4.70.

Example 4

Using the method of Example 3, but starting with cis-12-carbomethoxy-11-carboxy-9,10-dihydro-9,10-ethanoanthracene, the intermediate cis-11-(N-carbobenzyloxyamino)-12-carbomethoxy-9,10-dihydro-9,10-ethanoanthracene, m.p. 131°–134° C. (Analysis: Calculated for $C_{26}H_{23}NO_4$: %C, 75.4; %H, 5.6; %N, 3.4; Found: %C, 75.4; %H, 5.8; %N, 3.3.), is prepared and is further reacted as in Example 3 until cis-11-amino-12-carbomethoxy-9,10-dihydro-9,10-ethanoanthracene (m.p. 171°–174° C.) is obtained. When this product is dissolved in diethyl ether and treated with a solution of hydrogen chloride in isopropanol, a white solid is obtained which is recrystallized from isopropanol. Nuclear magnetic resonance spectral analysis supports the structural assignment of the carefully dried solid product, cis-11-amino-12-carbo-methoxy-9,10-dihydro-9,10-ethanoanthracene hydrochloride, m.p. 207°–208° C.

Analysis: Calculated for $C_{18}H_{17}NO_2HCl$: %C, 68.5; %H, 5.75; %N, 4.4. Found: %C, 68.1; %H, 5.90; %N, 4.3.

Other acid addition salts of this 11-amino derivative (or the corresponding trans compound), such as the acetate, sulfate, nitrate, propionate, etc., are readily formed by treating the base with equimolar amounts of the selected acid, as is well known to the art, in a suitable volatile solvent, followed by removal of the solvent as by evaporation.

Example 5

To a solution of trans-11-amino-12-carbomethoxy-9,10-dihydro-9,10-ethanoanthracene (19.3 g., 69.1 mmoles) in 75 ml. of acetic acid is added 14.4 g. of sodium nitrite (208.5 mmoles) in small portions over 2 hours, maintaining the temperature below about 50°C. The mixture is then stirred for about 16 hours at about 25° C. The mixture is evaporated under vacuum to remove acetic acid, and water and dichloromethane are added. The layers are separated, and the dichloromethane layer is washed with 2N hydrochloric acid, saturated sodium bicarbonate solution and saturated sodium chloride solution, then dried over anhydrous magnesium sulfate. Evaporation under vacuum provides an oil which is dissolved in 10 ml. of pyridine and 40 ml. of acetic anhydride by heating on a steam bath then allowed to stand at about 25° C. for one day. The mixture is evaporated under vacuum, then water and dichloromethane are added to the residue. The layers are separated, and the dichloromethane layer is washed with 2N hydrochloric acid, saturated sodium bicarbonate solution and saturated sodium chloride solution, then dried over anhydrous magnesium sulfate. Evaporation under vacuum provides 19.4 g. of solid, recrystallized from a benzenehexane mixture to give a product, m.p. 124°–135° C. Another recrystallization is carried out from benzene, then thorough drying gives m.p. 139°–141° C. for 11-exo-acetoxy-12-anti-carbomethoxy-10,11-dihydro-5,10-methano-5H-dibenzo[a,d]cycloheptene. Nuclear magnetic resonance and infrared spectral analysis confirm the structure.

Analysis: Calculated for $C_{20}H_{18}O_4$: %C, 74.5; %H, 5.6 Found: %C, 75.2; %H, 5.5.

Example 6

Using the method of Example 5, cis-11-amino-12-carbo-methoxy-9,10-dihydro-9,10-ethanoanthracene is converted by reaction with nitrous acid in acetic acid to 11-acetoxy-syn-12-carbomethoxy-10,11-dihydro-5,10-methano-5H-dibenzo[a,d]cycloheptene. This product is a mixture of exo and endo isomers at the 11 position. However, this product can be used without further purification as described in Example 9.

Example 7

To a solution of exo-11-acetoxy-2-anti-carbomethoxy-10,11-dihydro-5,10-methano-5H-dibenzo[a,d]cycloheptene (1.1 g.) in 50 ml. of acetic acid is added 0.5 g. of 10 percent palladium on charcoal and two drops of 70 percent perchloric acid. The mixture is treated with hydrogen gas at 50 psi at room temperature on a Paar apparatus for about 18 hours. The mixture is filtered, and the filtrate is evaporated under vacuum to provide a solid residue. The nuclear magnetic resonance spectrum is consistent with the structure assigned to the product, 12-anti-carbomethoxy-10,11-dihydro-5,10-methano-5H-dibenzo-[a,d]cycloheptene.

Example 8

The product of Example 7 is mixed with 5 percent sodium hydroxide and the mixture is heated on a steam bath for 2 hours. The mixture is poured into dilute hydrochloric acid, and the solid product which precipitates is separated by filtration. The nuclear magnetic resonance spectrum of the product corresponds to that of the known compound, anti-12-carboxy-10,11-dihydro-5,10-methano-5H-dibenzo[a,d]cycloheptene.

Example 9

A mixture of 100 ml. of aqueous 10 percent sodium hydroxide and 60 g. of 11-acetoxy-syn-carbomethoxy-10,11-dihydro-5,10-methano-5H-dibenzo[a,d]cycloheptene is stirred with intermittent heating at 50° C. for 23 hours. Diethyl ether is added, and the layers are separated. The aqueous layer is acidified with hydrochloric acid, the solid product is separated by filtration and washed with water. The solid product is 11-hydroxy-syn-12-carboxy-10,11-dihydro-5,10-methano-5H-dibenzo[a,d]cycloheptene.

Example 10

The product of Example 9 is mixed with 100 ml. of toluene and 0.2 g. of p-toluenesulfonic acid. The mixture is heated to its reflux temperature and maintained at reflux for 4 hours. The mixture is cooled to about 25° C., washed with saturated sodium bicarbonate solution and dried to provide exo-11-hydroxy-syn-12-carboxy-10,11-dihydro-5,10-methano-5H-dibenzo-[a,d]cycloheptene lactone. The structural assignment of the product is confirmed by infrared and nuclear magnetic resonance spectral analysis.

Example 11

To a solution of exo-11-hydroxy-syn-12-carboxy-10,11-dihydro-5,10-methano-5H-dibenzo[a,d]cycloheptene lactone (1.4 g.) in ethyl acetate is added 0.5 g. of palladium on charcoal, and the mixture is treated with hydrogen gas at about 25° C. on a Parr apparatus at about 45 psi. The mixture is filtered then evaporated under vacuum to provide 1.2 g. of the product, syn-12-carboxy-10,11-dihydro-5,10-methano-5H-dibenzo[a,d]cycloheptene. The structural assignment of the product is confirmed by infrared and nuclear magnetic resonance spectral analysis which are compared to the spectra of the known compound.

Example 12

Using the method of Example 3, trans-12-carbomethoxy-11-carboxy-9,10-dihydro-9,10-ethanoanthracene is converted to trans-11-azido-12-carbomethoxy-9,10-dihydro-9,10-ethanoanthracene which is converted to trans-11-(N-carbobenzyloxyamino)-12-carbomethoxy-9,10-dihydro-9,10-ethanoanthracene, m.p. 138°–140° C.

Analysis: Calculated for $C_{26}H_{23}NO_4$: %C, 75.4; %H, 5.6; %N, 3.4 Found: %C, 75.5; %H, 5.6; %N, 3.4.

Continuing with the method of Example 3, the intermediate is converted to trans-11-amino-12-carbomethoxy-9,10-di-hydro-9,10-ethanoanthracene. A portion of the product (5 g.) is dissolved with a mixture of isopropanol and isopropyl ether and is treated with 5 ml. of 8N hydrochloric acid in isopropanol. A white solid precipitates and is collected by filtration. Recrystallization provides the hydrochloride salt, m.p. 260°–262° C. (dec.).

Analysis: Calculated for $C_{18}H_{17}NO_2HCl$: %C, 68.5; %H, 5.75; %N, 4.44 Found: %C, 68.8; %H, 5.70; %N, 4.30.

The infrared and nuclear magnetic resonance spectra are consistent with the assigned structure.

What is claimed is:

1. Process for preparation of 12-carboxy-10,11-dihydro-5,10-methano-5H-dibenzo[a,d]cycloheptene, which comprises converting the maleic anhydride adduct of anthracene to the trans or cis form of 12-carboalkoxy-11-carboxy-9,10-dihydro-9,10-ethanoanthracene by reaction with a lower alkanol in the presence of strong base at a temperature in the range of 0° to 120° C., or with a lower alkanol alone at a temperature in the range of 60° to 120° C., respectively, and then carrying out the steps of:

1. reacting the 11-carboxyl group with a lower alkyl chloroformate in an inert solvent and in the presence of strong base at a temperature in the range of −20° to 10° C.;
2. treating the product of step (1) with aqueous alkali metal azide at a temperature in the range of −20° to 25° C.;
3. heating the product of step (2) at about 80° to 120° C. in an inert solvent;
4. reacting the product of step (3) with benzyl alcohol to form a cis- or trans-11-(N-carbobenzyloxyamino)-12-lower carboalkoxy-9,10-dihydro-9,10-ethanoantracene;
5. debenzylating the product of step (4) by catalytic hydrogenation at a temperature in the range of about 25° to 100° C. to form cis- or trans-11-amino-12-lower carboalkoxy-9,10-dihydro-9,10-ethanoanthracene;
6. treating the 11-amino compound of step (5) with nitrous acid in a protic solvent to form 11-lower acyloxy-, 11-hydroxy- or 11-alkoxy-12-syn- or anti-lower carboalkoxy-10,11-dihydro-5,10-methano-5H-dibenzo-[a,d]cycloheptene;
7. catalytically reducing the product of step (6) in inert solvent solution at a temperature in the range of 25° to 100° C. to remove the substituent in the 11 position;
8. subjecting the product of step (7) to hydrolysis to form syn- or anti-12-carboxy-10,11-dihydro-5,10-methano-5H-dibenzo[a,d]cycloheptene;

or alternatively, when starting with compounds of cis configuration:

9. converting 11-lower acyloxy- or 11-hydroxy-12-syn-lower carboalkoxy-10,11-dihydro-5,10-methano-5H-di-benzo[a,d]cycloheptene product of step (6) to the corresponding lactone and
10. catalytically reducing the lactone product of step (9) in inert solvent solution at a temperature in the range of 25° to 100° C. to form syn-12-carboxy-10,11-dihydro-5,10-methano- 5H-dibenzo[a,d]cycloheptene.

2. Process for preparation of 12-carboxy-10,11-dihydro-5,10-methano-5H-dibenzo[a,d]cycloheptene, which comprises converting the maleic anhydride adduct of anthracene to the trans or cis form of 12-carboalkoxy-11-carboxy-9,10-dihydro-9,10-ethanoanthracene by reaction with a lower alkanol in the presence of strong base at a temperature in the range of 0° to 120°C., or with a lower alkanol alone at a temperature in the range of 60° to 120°C., respectively, and then carrying out the steps of:

1. reacting the 11-carboxyl group with a lower alkyl chloroformate in an inert solvent and in the presence of strong base at a temperature in the range of −20 to 10°C.;
2. treating the product of step (1) with aqueous alkali metal azide at a temperature in the range of −20° to 25°C.;
3. heating the product of step (2) at about 80° to 120°C. in an inert solvent;
4. reacting the product of step (3) with benzyl alcohol to form a cis- or trans-11-(N-carbobenzyloxyamino)-12-lower carboalkoxy-9,10-dihydro-9,10-ethanoanthracene;
5. debenzylating the product of step (4) by catalytic hydrogenation at a temperature in the range of about 25° to 100°C. to form cis- or trans-11-amino-12-lower carboalkoxy-9,10-dihyro-9,10-ethanoanthracene;
6. treating the 11-amino compound of step (5) with nitrous acid in a protic solvent to form 11-alkoxy-12-syn- or anti-lower carboalkoxy-10,11-dihydro-5,10-methano-5H-dibenzo[a,d]-cycloheptene;
7. converting the 11- alkoxy group of the product of step 6 to hydroxy by ether cleavage;
8. catalytically reducing the product of step (7) in inert solvent solution at a temperature in the range of 25° to 100°C. to remove the substituent in the 11 position;
9. subjecting the product of step (8) to hydrolysis to form syn- or anti-12-carboxy-10,11-dihydro-5,10-methano-5H-dibenzo[a,d]cycloheptene.

3. Process according to claim 1, in which the 11-lower acyl-oxy- or 11-hydroxy-12-syn-lower carboalkoxy-10,11-dihydro-5,10-methano-5H-dibenzo[a,d]cycloheptene product of step (6) is converted to the corresponding lactone and catalytically reducing the lactone product of step (9) in inert solvent solution at a temperature in the range of 25° to 100° C. to form syn-12-carboxy-10,11-dihydro-5,10-methano-5H-dibenzo[a,d]cycloheptene.

4. In the process for making syn- or anti-12-carboxy-10,11-dihydro-5,10-methano-5H-dibenzo-[a,d]cycloheptene according to claim 1, the step which comprises treating cis- or trans-11-amino-12-lower carboalkoxy-9,10-dihydro-9,10-ethanoanthracene with nitrous acid in a protic solvent to form 11-lower acyloxy-, 11-hydroxy- or 11-alkoxy- 12-syn- or anti-lower carboalkoxy-10,11-dihydro-5,10-methano-5H-dibenzo[a,d]cycloheptene.

* * * * *